(12) United States Patent
Vukkadala et al.

(10) Patent No.: US 10,401,279 B2
(45) Date of Patent: Sep. 3, 2019

(54) PROCESS-INDUCED DISTORTION PREDICTION AND FEEDFORWARD AND FEEDBACK CORRECTION OF OVERLAY ERRORS

(71) Applicant: KLA-Tencor Corporation, Milpitas, CA (US)

(72) Inventors: Pradeep Vukkadala, Fremont, CA (US); Haiguang Chen, Mountain View, CA (US); Jaydeep Sinha, Livermore, CA (US); Sathish Veeraraghavan, Santa Clara, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 690 days.

(21) Appl. No.: 14/490,408

(22) Filed: Sep. 18, 2014

(65) Prior Publication Data

US 2015/0120216 A1    Apr. 30, 2015

Related U.S. Application Data

(60) Provisional application No. 61/897,208, filed on Oct. 29, 2013.

(51) Int. Cl.
  *G01B 5/28* (2006.01)
  *G01B 5/30* (2006.01)
  (Continued)

(52) U.S. Cl.
  CPC ............ *G01N 19/08* (2013.01); *C23C 14/54* (2013.01); *G01L 1/00* (2013.01); *G01L 5/0047* (2013.01);
  (Continued)

(58) Field of Classification Search
  CPC ............... G01N 19/08; G01N 21/9501; G01N 21/9505; G01L 1/00; G01L 5/0047; G03F 7/705; G03F 7/70633; G03F 7/70783
  (Continued)

(56) References Cited

U.S. PATENT DOCUMENTS 9,430,593 B2 *  8/2016  Vukkadala ........ H01L 21/67288
2005/0210438 A1  9/2005  Verstappen et al.
(Continued)

FOREIGN PATENT DOCUMENTS

JP    2009-099768 A    5/2009
JP    2010537394 A    12/2010
(Continued)

OTHER PUBLICATIONS

Turner et al., Monitoring Process-Induced Overlay Errors through High-Resolution Wafer Geometry Measurements, Proceedings of SPIE, vol. 9050, p. 905013-1-905013-9, Apr. 2, 2014, © 2014 SPIE.
(Continued)

*Primary Examiner* — Michael P Nghiem
(74) *Attorney, Agent, or Firm* — Suiter Swantz pc llo (57) ABSTRACT

Systems and methods for prediction and measurement of overlay errors are disclosed. Process-induced overlay errors may be predicted or measured utilizing film force based computational mechanics models. More specifically, information with respect to the distribution of film force is provided to a finite element (FE) model to provide more accurate point-by-point predictions in cases where complex stress patterns are present. Enhanced prediction and measurement of wafer geometry induced overlay errors are also disclosed.

25 Claims, 10 Drawing Sheets

(51) Int. Cl.
*G01N 19/08* (2006.01)
*G01L 1/00* (2006.01)
*H01L 21/66* (2006.01)
*G01L 5/00* (2006.01)
*G03F 7/20* (2006.01)
*C23C 14/54* (2006.01)

(52) U.S. Cl.
CPC .......... *G03F 7/705* (2013.01); *G03F 7/70633* (2013.01); *G03F 7/70783* (2013.01); *H01L 22/12* (2013.01); *H01L 22/20* (2013.01)

(58) Field of Classification Search
USPC ........................................................ 702/35
See application file for complete search history.

(56) References Cited

U.S. PATENT DOCUMENTS

| | | | |
|---|---|---|---|
| 2006/0123919 | A1 | 6/2006 | Lovell et al. |
| 2007/0198967 | A1 | 8/2007 | Ren et al. |
| 2008/0057418 | A1* | 3/2008 | Seltmann ............ G03F 7/70633 430/30 |
| 2008/0199978 | A1 | 8/2008 | Fu et al. |
| 2008/0316442 | A1* | 12/2008 | Adel .................. G03F 7/70258 355/52 |
| 2011/0172982 | A1 | 7/2011 | Veeraraghavan et al. |
| 2012/0208301 | A1 | 8/2012 | Izikson et al. |
| 2013/0060354 | A1* | 3/2013 | Choi ................ G05B 19/41875 700/51 |
| 2013/0089935 | A1 | 4/2013 | Vukkadala et al. |
| 2014/0107998 | A1 | 4/2014 | Vukkadala et al. |

FOREIGN PATENT DOCUMENTS

| | | | |
|---|---|---|---|
| JP | 2013527972 A | | 7/2013 |
| TW | 201245896 A | | 11/2012 |
| TW | 201308463 A | | 2/2013 |
| TW | 201334145 A | | 8/2013 |
| TW | 201322353 A | | 5/2016 |
| WO | WO 2015/066232 | * | 5/2015 |

OTHER PUBLICATIONS

Turner et al., Relationship between localized wafer shape changes induced by residual stress and overlay errors, Journal of Micro/Nanolithography, MEMS, and MOEMS, vol. 11, Issue 1, Jan.-Mar. 2012, pp. 013001-1-313001-8, © 2012 SPIE.
G.G. Stoney et al., The Tension of Metallic Films deposited by Electrolysis, Proc. Royal Soc. London, A82, pp. 172-175, Feb. 4, 1909.
Timothy A. Brunner et al., Characterization of wafer geometry and overlay error on silicon wafers with nonuniform stress, J. Micro/Nanolith. MEMS MOEMS 12(4), 043002 (Oct.-Dec. 2013), published online Oct. 25, 2013, pp. 043002-1-043002-12.
PCT International Search Report, International Application No. PCT/US2014/062992, dated Jan. 28, 2015.
Kevin T. Turner et al., Predicting distortions and overlay errors due to wafer deformation during chucking on lithography scanners, J. Micro/Nanolith. MEMS MOEMS vol. 8(4), 043015 (Oct.-Dec. 2009), © 2009 SPIE, 8 pages.
Sathish Veeraraghaven et al., Simulation of non-uniform wafer geometry and thin film residual stress on overlay errors, Metrology, Inspection, and Process Control for Microlithography XXV, SPIE, Bellingham, WA, USA, vol. 7971, No. 1, Mar. 17, 2011, pp. 1-6.
JP Office Action dated Apr. 24, 2018 for Japanese Patent Application No. 2016-526795.

* cited by examiner

PROCESS-INDUCED DISTORTION PREDICTION AND FEEDFORWARD AND FEEDBACK CORRECTION OF OVERLAY ERRORS

CROSS-REFERENCE TO RELATED APPLICATIONS

The present application claims the benefit under 35 U.S.C. § 119(e) of U.S. Provisional Application Ser. No. 61/897,208, filed Oct. 29, 2013. Said U.S. Provisional Application Ser. No. 61/897,208 is hereby incorporated by reference in its entirety.

TECHNICAL FIELD

The disclosure generally relates to the field of wafer surface metrology, and particularly to systems and methods for prediction of process-induced distortions.

BACKGROUND

Thin polished plates such as silicon wafers and the like are a very important part of modern technology. A wafer, for instance, may refer to a thin slice of semiconductor material used in the fabrication of integrated circuits and other devices. Other examples of thin polished plates may include magnetic disc substrates, gauge blocks and the like. While the technique described here refers mainly to wafers, it is to be understood that the technique also is applicable to other types of polished plates as well. The term wafer and the term thin polished plate may be used interchangeably in the present disclosure.

Fabricating semiconductor devices typically includes processing a substrate such as a semiconductor wafer using a number of semiconductor fabrication processes. For example, lithography is a semiconductor fabrication process that involves transferring a pattern from a reticle to a resist arranged on a semiconductor wafer. Additional examples of semiconductor fabrication processes include, but are not limited to, chemical-mechanical polishing (CMP), etching, deposition, and ion implantation.

Generally, certain requirements are established for the flatness and thickness uniformity of the wafers. However, the various process steps required during fabrication and thickness variations result in elastic deformation that can cause significant distortions (e.g., in-plane distortions IPD and/or out-plane distortions OPD). Distortions may lead to errors in downstream applications such as overlay errors in lithographic patterning or the like. Therefore, providing the ability to predict/estimate process-induced distortions is a vital part of semiconductor manufacturing process.

Therein lies a need for systems and methods for accurate and efficient prediction and measurement of distortions.

SUMMARY

The present disclosure is directed to a method. The method includes: obtaining a first set of wafer geometry measurements of a wafer prior to the wafer undergoing a fabrication process; obtaining a second set of wafer geometry measurements of the wafer after the fabrication process; calculating a film force distribution on the wafer based on the first set of wafer geometry measurements and the second set of wafer geometry measurements; and utilizing a finite element (FE) model to estimate at least one of: an out-plane distortions (OPD) and an in-plane distortions (IPD) of the wafer at least partially based on the calculated film force distribution.

A further embodiment of the present disclosure is also directed to a method. The method includes: generating a series of basis film force distribution maps; performing finite element (FE) model based overlay error prediction for each particular film force distribution map of the series of basis film force distribution maps; storing each particular film force distribution map of the series of basis film force distribution maps and the overlay error predicted for that particular film force distribution map; and utilizing the stored basis film force distribution maps and the overlay errors predicted for the stored basis film force distribution maps to estimate overlay error of a given wafer.

An additional embodiment of the present disclosure is directed to a system for providing distortion prediction for a wafer. The system includes: a geometry measurement tool configured to obtain a first set of wafer geometry measurements of the wafer prior to the wafer undergoing a fabrication process and to obtain a second set of wafer geometry measurements of the wafer after the fabrication process. The system also includes a finite element (FE) model based prediction processor in communication with the geometry measurement tool. The FE model based prediction processor is configured to: calculate a film force distribution on the wafer based on the first set of wafer geometry measurements and the second set of wafer geometry measurements; and estimate at least one of: an out-plane distortions (OPD) and an in-plane distortions (IPD) of the wafer at least partially based on the calculated film force distribution.

An additional embodiment of the present disclosure is directed to a method. The method includes: acquiring shape and thickness maps of a wafer before and after the wafer being processed by a wafer process tool; calculating shape and thickness difference maps based on shape and thickness maps of the wafer acquired before and after the wafer being processed by the wafer process tool; extracting slope, curvature and at least one higher order differential component from the shape and thickness difference maps; and calculating an overlay error induced by the wafer process tool at least partially based on: the slope, the curvature and the at least one higher order differential component from the shape and thickness difference maps.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

The development and usage of a finite element (FE) model based distortion prediction is described in: Predicting distortions and overlay errors due to wafer deformation during chucking on lithography scanners. Kevin Turner et al., Journal of Micro/Nanolithography, MEMS, and MOEMS, 8(4), 043015 (October-December 2009), and more recently, in: Relationship between localized wafer shape changes induced by residual stress and overlay errors, Kevin Turner et al., Journal of Micro/Nanolithography, MEMS, and MOEMS, 11, 013001 (2012), which are both herein incorporated by reference. The FE model based distortion prediction utilizes full-scale 3-D wafer and chuck geometry information and simulates the non-linear contact mechanics of the wafer chucking mechanism, allowing the FE model to provide prediction of distortions (e.g., OPD and IPD) of the wafer surface. IPD is obtained by taking the full in-plane distortions of the wafer (either output by the FE model or by some other method) and applying linear-corrections to it, such as the 10-term correction that emulates alignment/overlay corrections applied by the lithography scanner during wafer exposure.

The FE model may also be emulated utilizing a combination of analytical and empirical method. The development and usage of an emulated FE model is described in: System and method to emulate finite element model based prediction of in-plane distortions due to semiconductor wafer chucking, P. Vukkadala et al., U.S. Pat. No. 9,430,593, , which is herein incorporated by reference in its entirety.

While the existing FE model based distortions and overlay errors prediction methods provide good sensitivity to process-induced overlay errors in several cases, they may lack accurate point-by-point predictions in some practical cases where complex stress patterns are present on the wafers. Embodiments of the present disclosure overcome these shortcomings by providing systems and methods utilizing film force based computational mechanics models to produce distortion and overlay predictions. More specifically, information with respect to the distribution of film force is provided to an FE model to provide more accurate point-by-point predictions in cases where complex stress patterns are present.

In accordance with embodiments of the present disclosure, film force is defined as the product of stress and thickness. The advantage of using film force is that it can describe both stress and thickness variations of the film. It is noted that since much of the force variation that one might be concerned with in overlay applications is due to local etching (removal of film), it is therefore important for the film force to include this effect. A detailed explanation of film force is described in: Monitoring process-induced overlay errors through high resolution wafer geometry measurements, Kevin Turner et al., Proceedings of SPIE, Vol. 9050, p. 905013, 2014, which is herein incorporated by reference in its entirety.

It is also noted that film force may change due to processing (e.g., film deposition or the like). It is therefore important to take wafer geometry measurements in order to determine any film force changes.

Figure 1:
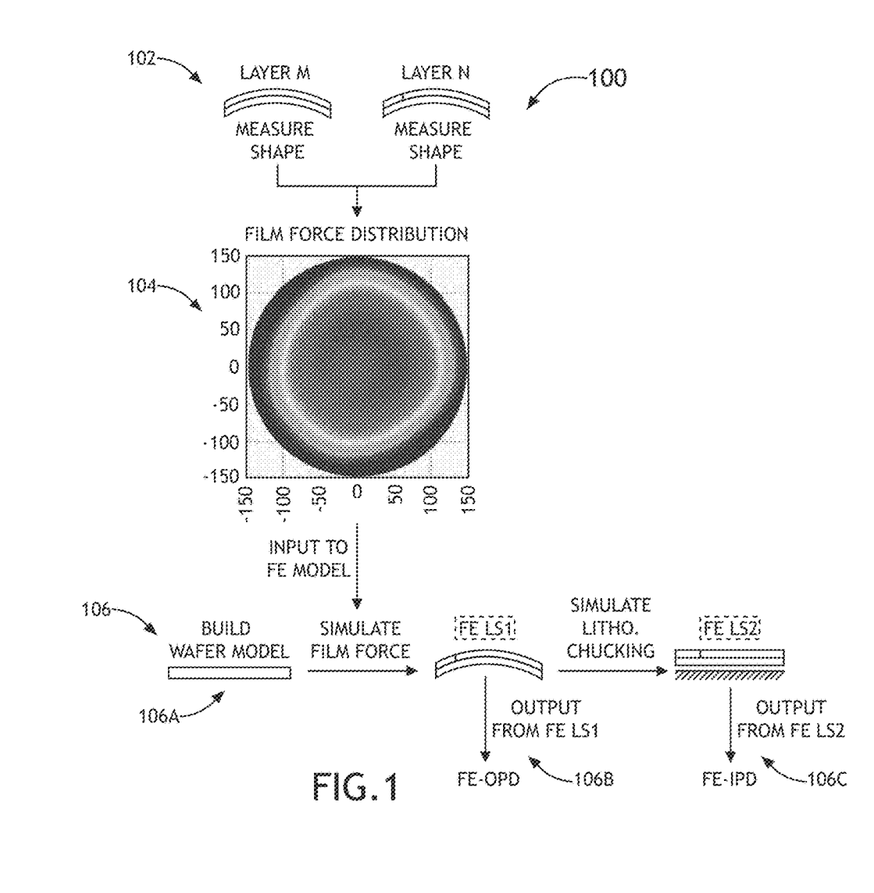
FIG. 1 is an illustration depicting a method utilizing a film force based finite-element (FE) model for distortion and/or overlay error prediction.

Referring to FIG. 1, a film force based finite-element (FE) model 100 for distortion prediction is shown. In step 102, wafer geometry measurements are taken prior to and after a fabrication process step (e.g., a patterning step or the like). For illustrative purposes, geometry measurements taken prior to the process step are denoted as Layer M measurements, and geometry measurements taken after the process step are denoted as Layer N measurements. In some embodiments, geometry measurements are taken when the wafer is in its free state. Taking wafer geometry measurements in its free state prior to and after a process step allows changes in wafer geometry due to processing to be determined.

The wafer geometry measurements taken both prior to and after the process step are then provided to a film force distribution processor in step 104, which is configured to calculate distribution of film force based on the wafer geometry measurements. In some embodiments, film force (per unit depth) is determined as a product of film stress and film thickness, and the distribution of film force throughout the entire wafer can be calculated accordingly. An advantage of using film force is that it can describe both stress and thickness variations of the film either of which can affect local distortions on the wafer that may lead to overlay errors.

It is contemplated that various methods may be utilized to estimate the film stress. For instance, a stress/deflection relationship, such as that expressed in the Stoney's equation or the like, may be utilized for calculating film stress based on the wafer geometry measurements. Stoney's equation is disclosed in: *The Tension of Metallic Films Deposited by Electrolysis*, G. G. Stoney, Proc. Royal Soc. London, A82, 172 (1909), which is herein incorporated by reference in its entirety. The Stoney's equation gives the stress in the film, $\sigma_f$, as a function of the film thickness, $h_f$, substrate thickness, $h_s$, biaxial modulus of the substrate, $$\sigma_f = \frac{1}{6} \frac{\overline{E}_s h_s^2}{h_f} k$$

where $E_s$ and $v_s$ are the Young's modulus and Poisson's ratio of the substrate, and the curvature, k, as:

$$\overline{E}_s, \left( \overline{E}_s = \frac{E_s}{1 - v_s} \right),$$

It is noted that the curvature may be obtained from the changes in wafer geometry (front surface or back surface or wafer shape information) measured by the geometry measurement tool. Other parameters such as film thickness and substrate thickness may also be measured. However, if they are not readily available, assumed values may be used to instead. In cases where assumed values are used during stress calculation, the same assumed values for these parameters must be used in the later steps, including the FE modeling process.

Once the distribution of film force is calculated, this information can be provided to an FE model in order to predict distortions and overlay errors in step 106. As previously described, FE and/or emulated FE models (jointly referred to as FE models) are non-linear models that are used to predict distortions and overlay errors due to wafer deformation. More specifically, as depicted in step 106, a wafer model 106A is built to represent a wafer, which initially may not be under any stress. This wafer model 106A may realistically represent the wafer stiffness and/or other mechanical properties. Subsequently, film force distribution calculated in step 104 is provided to the FE model, which may simulate the film force applied to the wafer model 106A, resulting in a wafer model 106B. This wafer model 106B may be utilized for out-plane distortion OPD calculation, and subsequently, the FE model may simulate the effects of wafer chucking applied to the wafer model 106B, resulting in a simulated chucked wafer model 106C. This wafer model 106C may then be utilized for in-plane distortion IPD calculation.

It is contemplated that the film force based FE model can also be configured to operate across more than one process tool. More specifically, referring to FIG. 2, another film force based FE model 200 for distortion prediction is shown. The method steps labeled 202 generally coincide with the method steps depicted in FIG. 1. That is, wafer geometry measurements are taken prior to and after a first wafer process. For illustrative purposes, geometry measurements of the wafer taken prior to the first wafer process are denoted as Layer M measurements, and geometry measurements of the wafer taken after the first wafer process are denoted as Layer N measurements. Subsequently, the method steps for film force estimation and distortion calculation are performed similarly to their corresponding steps depicted in FIG. 1. In this manner, the FE model is able to generate wafer IPD and/or OPD predictions based on measurements taken before and after the first wafer process.

Figure 2:
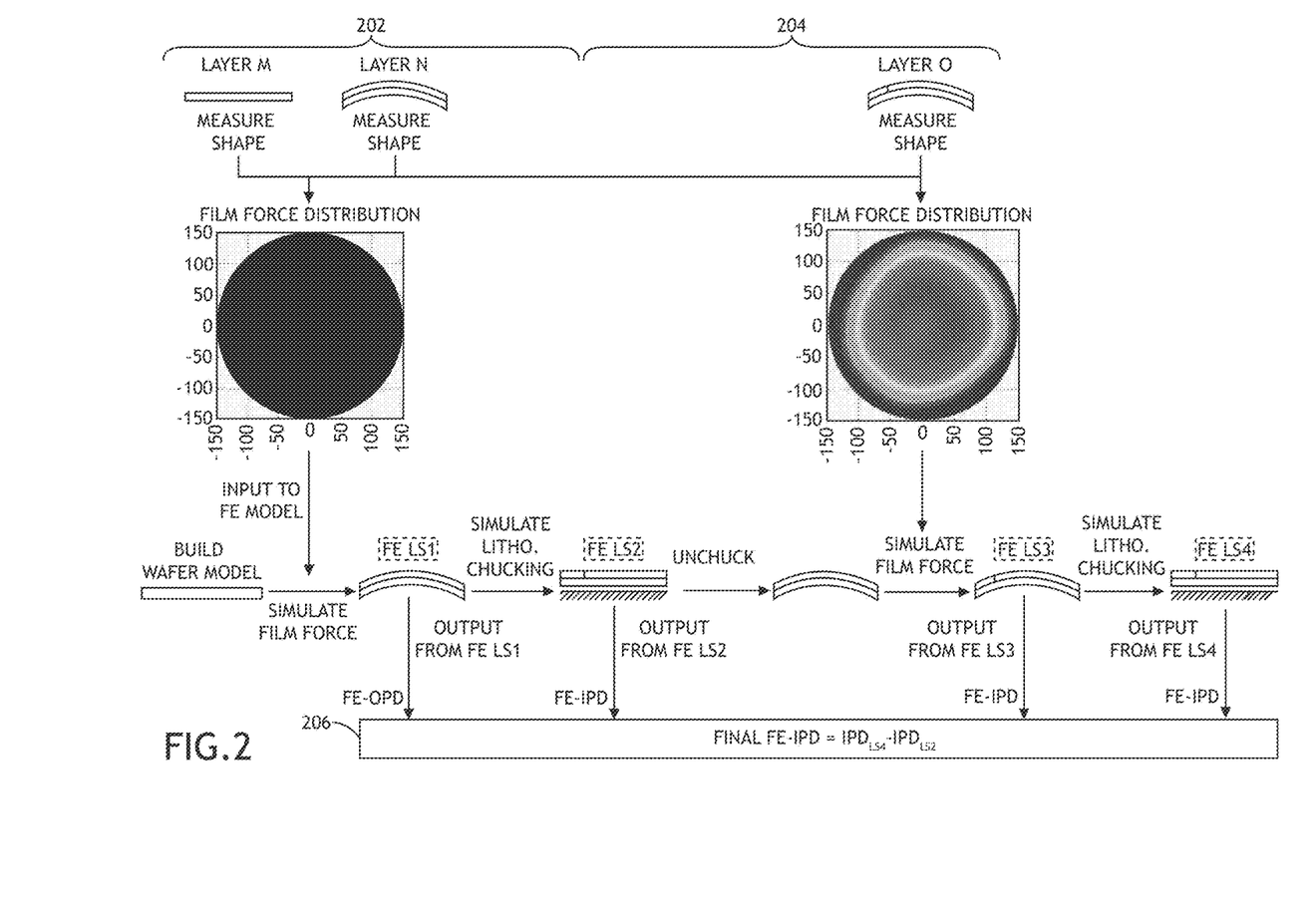
FIG. 2 is an illustration depicting another method utilizing a film force based FE model for distortion and/or overlay error prediction.

It is noted that upon completion of the first wafer process, the wafer may be unchucked from the first process tool and a second wafer process may follow. The FE model 200 is used again to generate wafer IPD and/or OPD predictions based on measurements taken before and after the second wafer process. That is, the method steps labeled 204 again generally coincide with the method steps depicted in FIG. 1. For illustrative purposes, geometry measurements of the wafer taken prior to the second wafer process (i.e., the same as the measurements taken after the first wafer process) are denoted as Layer N measurements, and geometry measurements of the wafer taken after the second wafer process are denoted as Layer O measurements. Subsequently, the method steps for film force estimation and distortion calculation are performed similarly to their corresponding steps depicted in FIG. 1.

At this point, two sets of IPD predictions and/or two sets of OPD predictions may be obtained. An additional step 206 may be utilized to consolidate the IPD predictions and/or the OPD predictions based on the predictions provided in steps 202 and 204. For instance, a consolidated IPD prediction may be calculated as the difference between the IPD prediction provided by step 202 and the IPD prediction provided by step 204. Similarly, a consolidated OPD prediction may be calculated as the difference between the OPD prediction provided by step 202 and the OPD prediction provided by step 204.

It is contemplated that regardless of whether the predictions are generated based on wafer geometry measurements taken prior to and after a single process step (e.g., FIG. 1) or multiple process steps (e.g., FIG. 2), the prediction results can be utilized to predict wafer distortions and/or overlay errors that may occur in a subsequent process during which the wafer may be chucked flat (e.g., a lithography process). The ability to make such predictions may be appreciated in various downstream applications, such as monitoring and/or controlling overlay errors that may occur during semiconductor manufacturing.

More specifically, an overlay error is a misalignment between any of the patterns used at different stages of semiconductor manufacturing. During a lithography process, for example, the wafer is held on a vacuum or electrostatic chuck using force. When the wafer is held in such a manner, the shape of the wafer changes compared to the wafer in its free state. The combination of wafer geometry changes and chucking causes overlay errors between process steps M and N.

Figure 3:
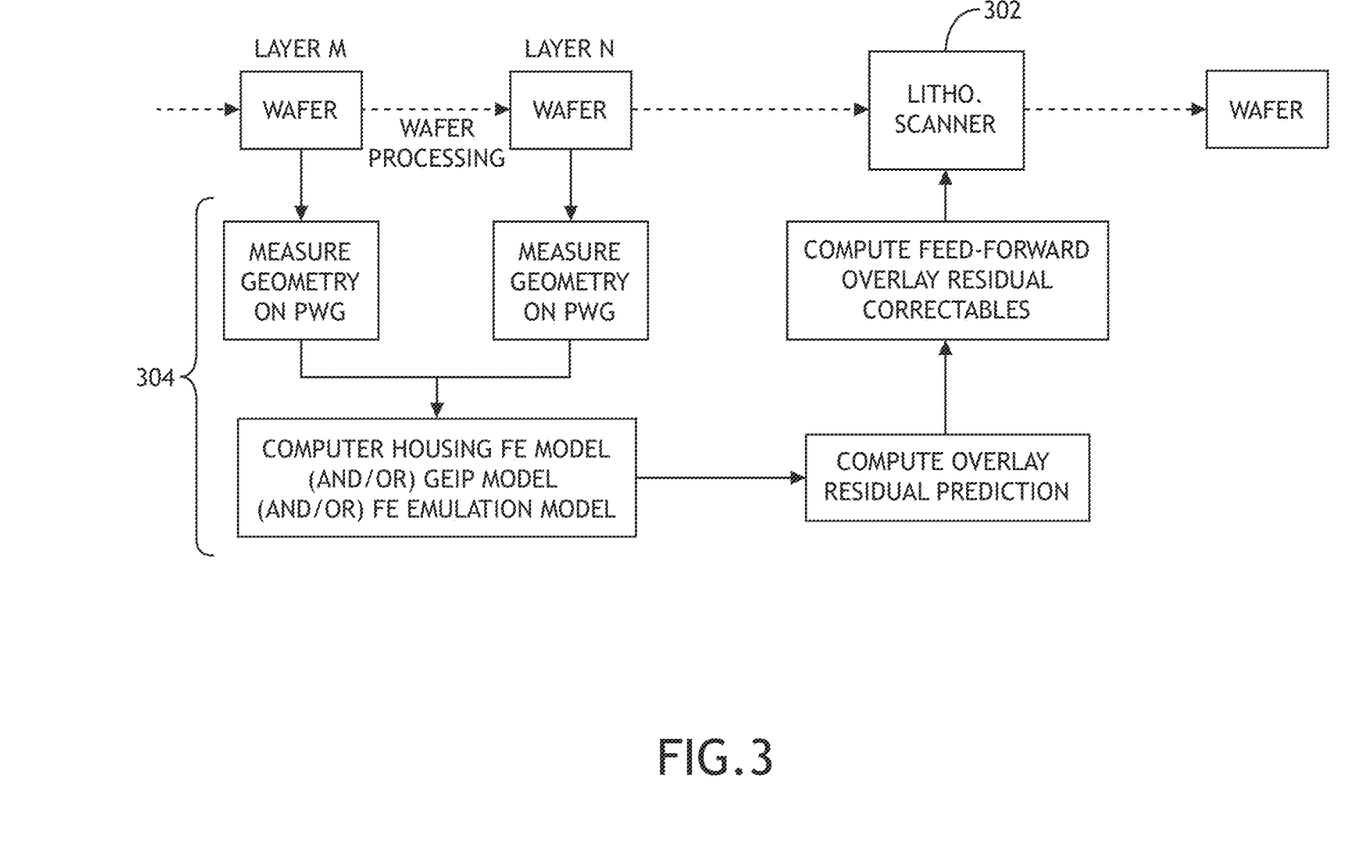
FIG. 3 is a block diagram depicting a feedforward control loop based on distortion and/or overlay error prediction.

Referring now to FIG. 3, a process tool 302 (such as a lithography scanner) controlled utilizing a feedforward loop 304 is shown. In one embodiment, measurements from one or more previous process steps are taken and fed to an FE model utilized for IPD prediction as described above. The IPD prediction generated by the FE model is then provided to a processor to calculate corrections that are needed to align the wafer during the lithography process in order to minimize potential misalignment that is predicted to occur. The correction values calculated in this manner can be provided to the lithography scanner 302 prior to the lithography process and the potential misalignment and overlay errors can be mitigated.

Figure 4:
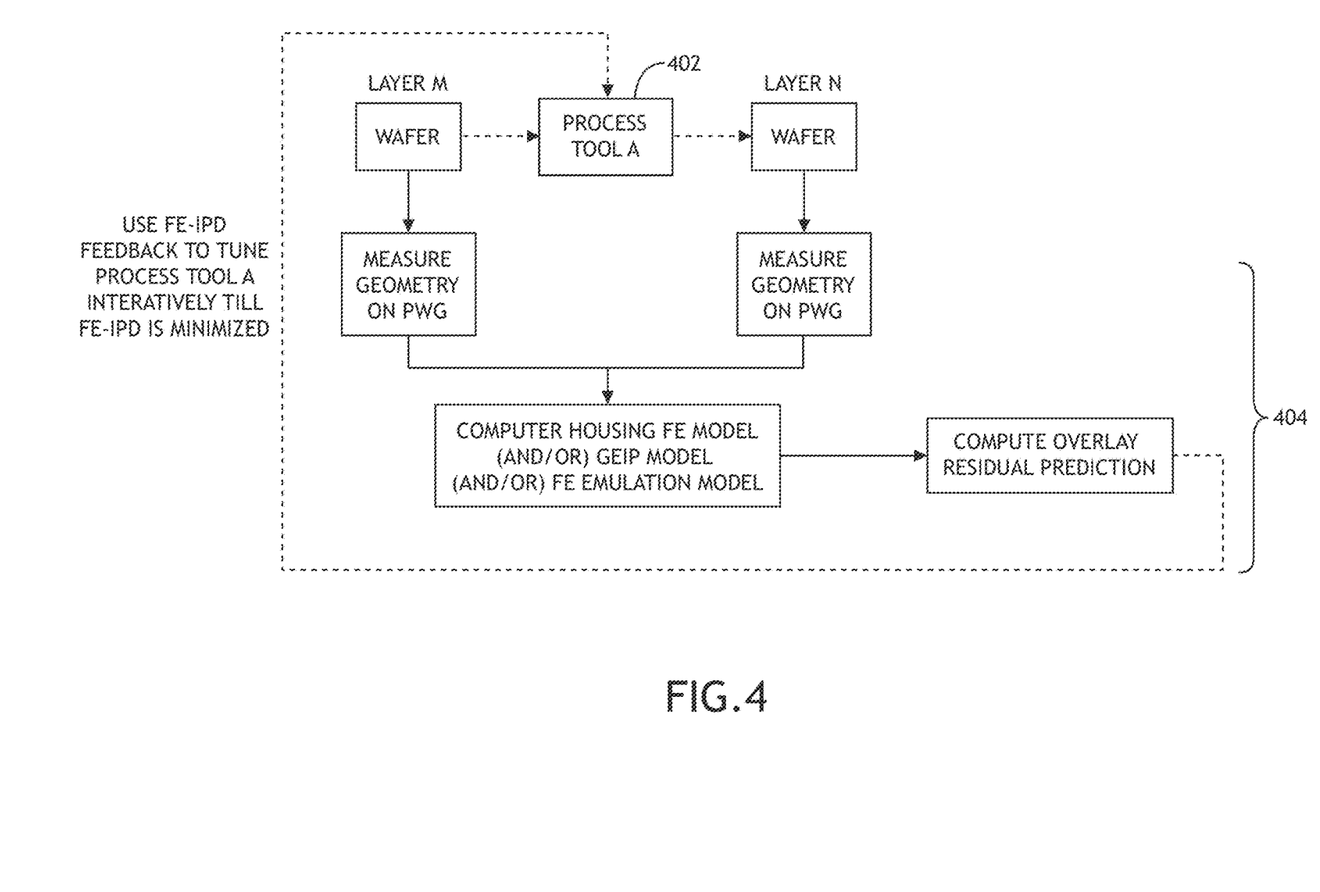
FIG. 4 is a block diagram depicting a feedback control loop based on distortion and/or overlay error measurement.

In addition, overlay errors can also be used in a feedback loop to improve the performance of a process tool. FIG. 4 shows a block diagram of a process tool 402 utilizing such a feedback loop 404. More specifically, measurements are taken both before and after the handling of the wafer by the process tool 402. These measurements are processed by the FE model utilized for IPD measurements as described above. The measured IPD generated by the FE model is then provided back to the process tool 402 in order to tune the process tool 402 iteratively until the IPD provided in the feedback loop is minimized.

It is contemplated that the feedforward and the feedback control loops described above are merely exemplary. The ability to provide efficient prediction/measurement of the wafer distortions may be beneficial to various downstream process tools without departing from the spirit and scope of the present disclosure.

It is also noted that the performance of the FE model for predicting IPD/overlay is dependent on the accuracy of the film force (product of stress and thickness) distribution that is fed into the FE model. As previously described, film force can be estimated/calculated in step 104 from the measured geometry data using analytical models such as Stoney's equation or the like. It is contemplated that the accuracy provided by such analytical methods may be further improved.

In one embodiment, for instance, an iterative approach is utilized to improve the accuracy of the film force distribution from measured wafer geometry data. This iterative approach may also be used to calculate film force for wafers with large deformations.

Figure 5:
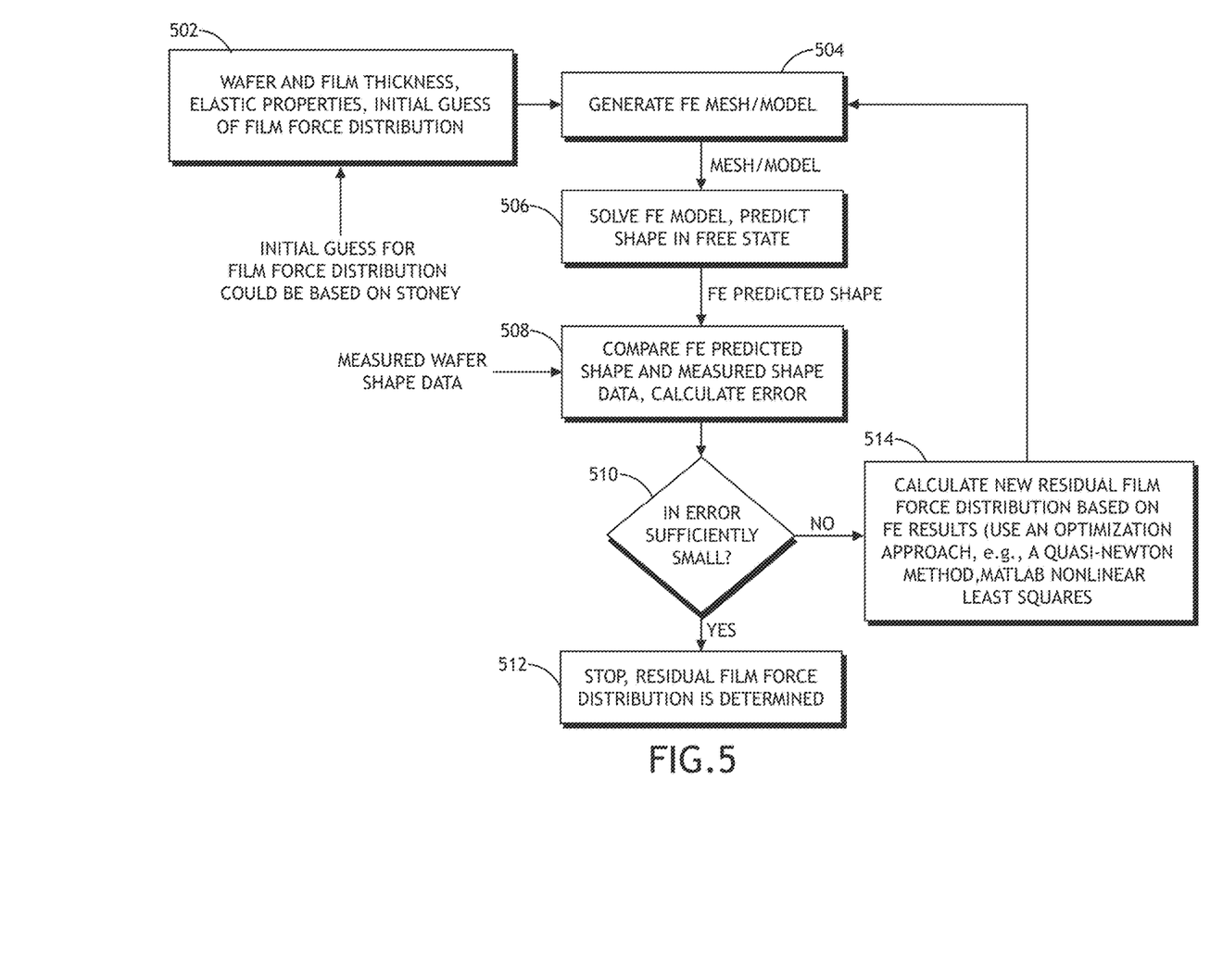
FIG. 5 is a flow diagram depicting a method for iteratively improving accuracy of a film force distribution calculation.

Referring now to FIG. 5, a method 500 to iteratively improve the accuracy of the film force distribution calculation is shown. As depicted in the figure, an initial calculation of the film force distribution is performed in step 502. This initial calculation of the film force distribution may be calculated in a manner similar to step 104 previously described (e.g., based on Stoney's equation or the like). Subsequently, the initial film force distribution, along with wafer and film thickness data and elastic properties, are utilized to construct an FE model in step 504 and the FE model constructed in this manner can be utilized to calculate the shape of the wafer in its free state in step 506. The shape of the wafer calculated using the FE model is then compared to measured wafer shape data in step 508. If it is determined in step 510 that the differences (i.e., errors) between the calculated and the measured shape data are small enough (i.e., below a predetermined threshold), the film force distribution calculation is completed in step 512 and the determined film force distribution is utilized as input to step 106 for distortions and overlay errors prediction. On the other hand, if it is determined in step 510 that the differences (i.e., errors) between the calculated and the measured shape data are not sufficiently small, further improvements are needed.

As indicated in step 514, a new film force distribution is calculated and the method 500 repeats again from step 504. It is contemplated that various methods can be utilized to calculate and/or optimize the new film force distribution without departing from the spirit and scope of the present disclosure. For instance, a quasi-Newton method or the like may be suitable to carry out this calculation process.

It is further contemplated that in addition to improving the accuracy of the film force distribution calculation (i.e., the input to the FE model) in an effort to improve the prediction accuracy, another enhancement may be directed towards further improving the computational efficiency of the FE model. In one embodiment, the computational efficiency of the FE model is improved by carrying out the operations in two stages: an off-line FE model training stage and an on-line IPD error prediction stage.

Figure 6:
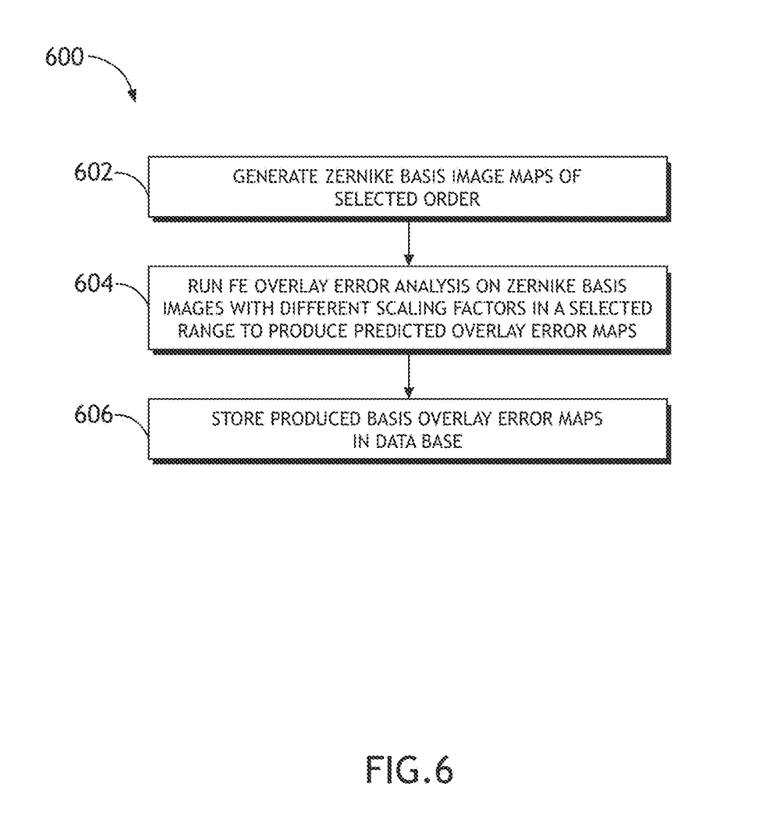
FIG. 6 is a flow diagram depicting a method for enhanced overlay error prediction.

Referring to FIG. 6, at the off-line training stage, a set of selected or system generated basis force distribution maps (step 602) are inputted to the FE model to obtain the corresponding overlay error images (step 604). These basis overlay error images may then be saved in a database (step 606). Depending on the wafer surface properties, different basis images can be used to obtain the most efficient image representation. For example, for the smoother wafer surface, the Zernike basis images can be used, while for the wafer surface with strong periodic patterns, Cosine basis images can be utilized. It is noted that the basis images obtained from Zernike transform and/or Cosine transform are real images and are thus well suited for decomposition of the force distribution map.

Figure 7:
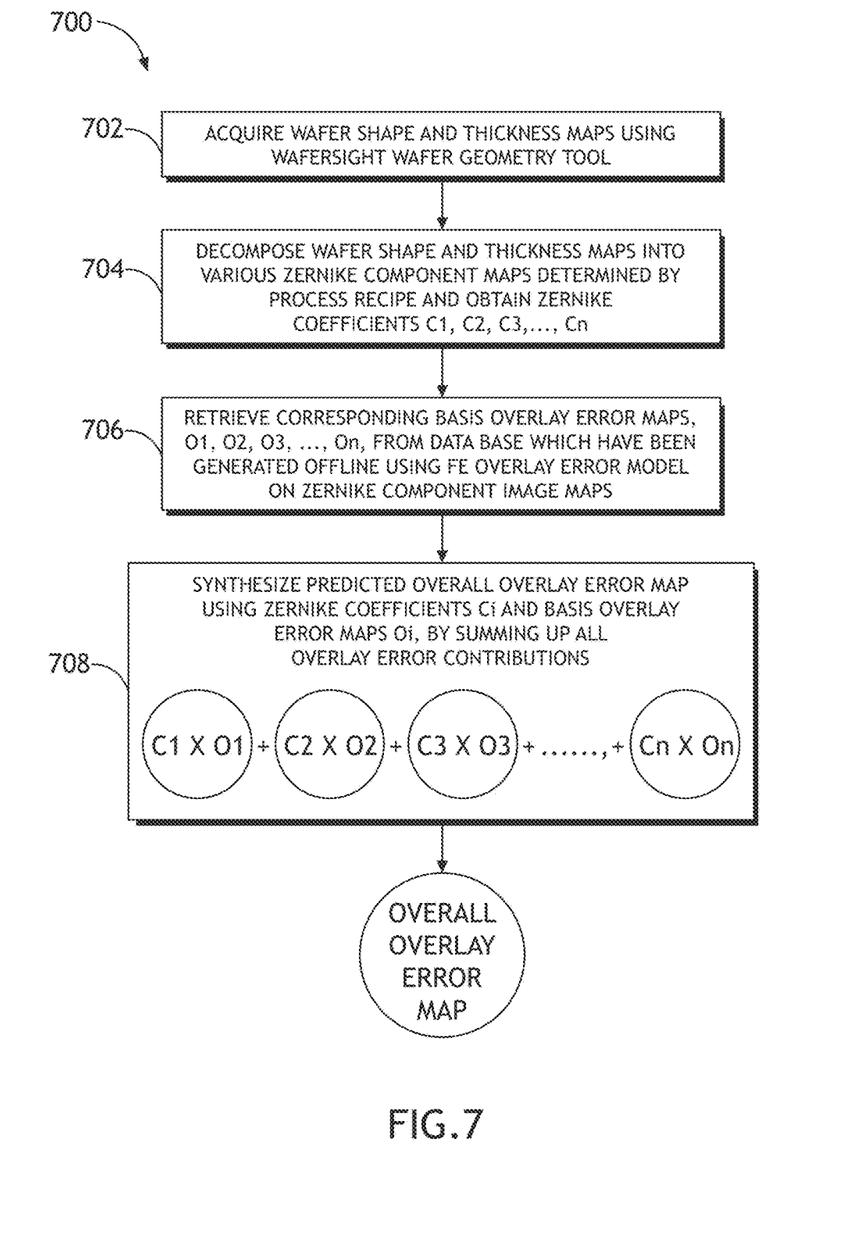
FIG. 7 is a flow diagram depicting an off-line FE model training method.
Figure 8:
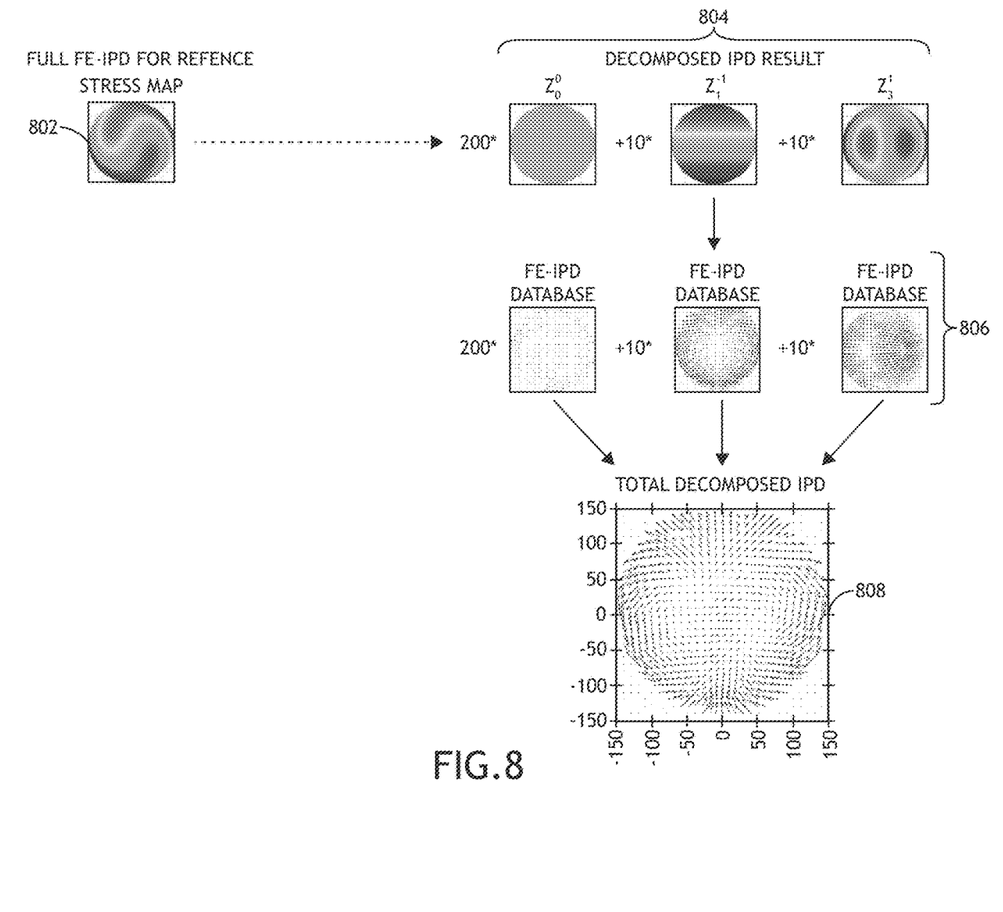
FIG. 8 is an illustration depicting error prediction utilizing an off-line trained model.

Subsequently, at the on-line IPD error prediction stage depicted in FIGS. 7 and 8, after the force distribution (may also be referred to as the stress map) 802 of the wafer is calculated (step 702), the force distribution 802 can be quickly decomposed into the linear summation of the basis force distribution maps 804 by solving linear equations for Zernike coefficients or by performing the Cosine transform for Cosine coefficients (step 704). The corresponding overlay error images 806 from these major basis images can be retrieved from the database (step 706) and scaled according to their amplitudes. These overlay error images 806 can then be synthesized (e.g., accumulated) to form a complete overlay error prediction image 808 (step 708).

It is noted that since the three required operations: (1) image retrieval from the hard disk, (2) image scaling and (3) image accumulation, can be carried out very efficiently, this on-line IPD error prediction process can significantly reduce the execution time to provide accurate overlay error prediction at the throughput required by on-line chip production.

Another advantage of this two-staged process is that re-training can be performed off-line and the on-line IPD error prediction process can be updated by simply updating the overlay error image database. Re-training may be performed whenever improvements are made (e.g., using a new or an improved FE model), and the overlay error image database generated utilizing the new FE model can be quickly updated and the improvements can be reflected at the on-line error prediction stage. In this manner, no software/firmware changes are needed, and database updates can be carried out easily offline in parallel by sending the selected basis images through the new FE model developed.

Figure 9:
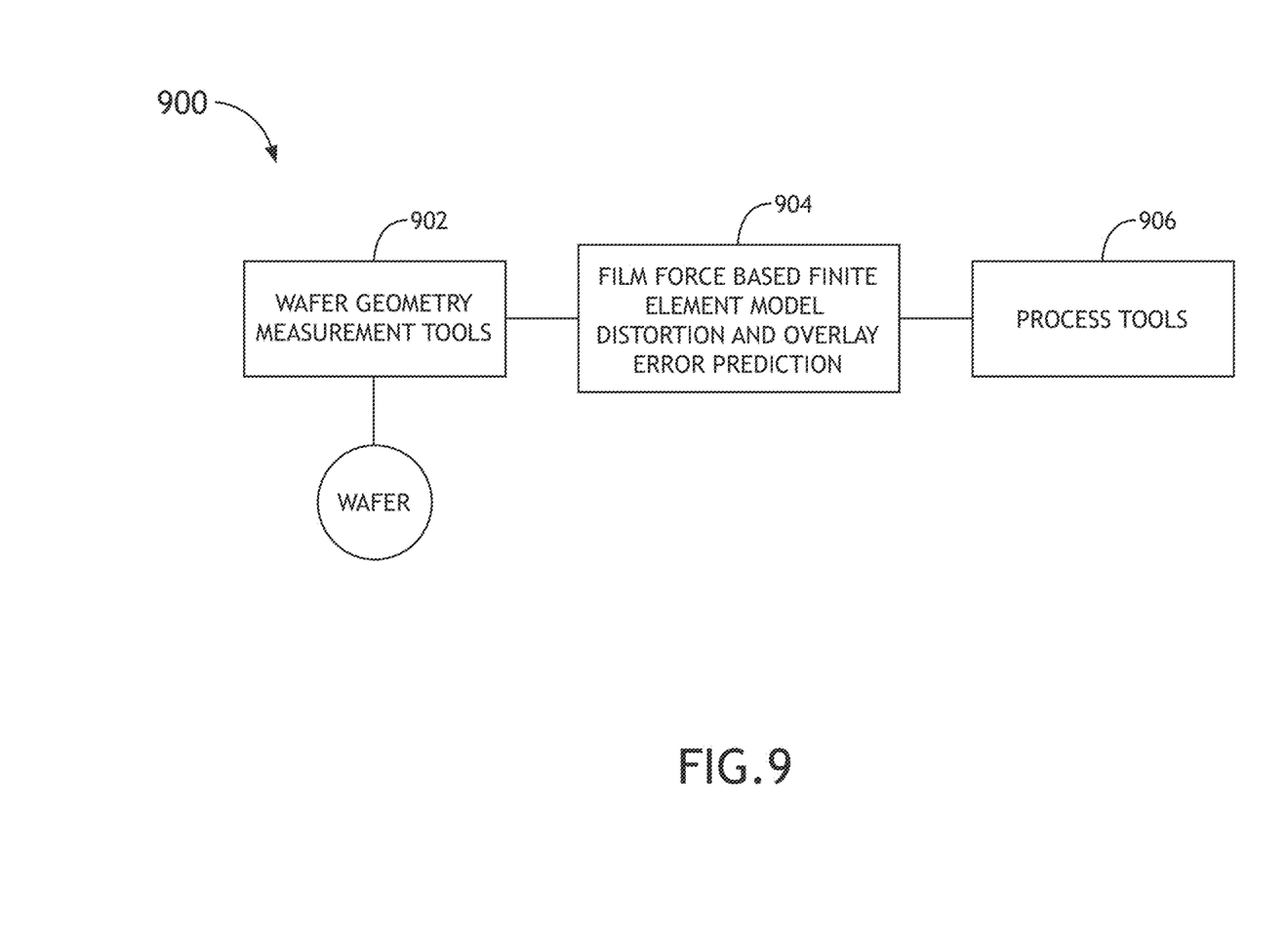
FIG. 9 a block diagram depicting a system utilizing a film force based FE model for distortion and/or overlay error prediction.

FIG. 9 is a block diagram depicting a system 900 utilizing a film force based FE model for distortion and overlay error predictions as described above. It is contemplated that the film force based FE model prediction processor 904 may be implemented as a standalone processing device or as an embedded/integrated component of the wafer geometry measurement tool 902. The wafer geometry measurement tool 902 may monitor the geometry of a given wafer and utilize the distortion and overlay error predictions to control various process tools 906, including, but not limited to, lithography focus control, CMP, as well as other semiconductor process control scanner corrections.

It is further completed that additional/alternative processes may also be utilized to predict/measure wafer geometry induced overlay errors. In one embodiment, for instance, wafer geometry induced overlay error predictions can be predicted/measured by taking more wafer shape and thickness components into consideration. More specifically, a typical overlay error prediction first calculates a difference map from two shape maps obtained and then the X and Y slope components from this shape difference map are used to predict the overlay error. The overlay errors in X and Y directions may be calculated from the X and Y slope of shape change residue components, $SSCR_x$ and $SSCR_y$, respectively as:

$$OverlayError_x = k_x \times SSCR_x$$

$$OverlayError_y = k_y \times SSCR_y$$

It is noted that the slope of shape change residue components, or SSCRs, are defined in: U.S. Pat. App. No. 2013/0089935, the disclosures of which is incorporated herein by reference in its entirety. The term "residue" here refers to the removal of linear components. More specifically, for SSCR, residue refers to the application of a linear correction such as the correction techniques described in U.S. Pat. App. No. 2013/0089935.

It is noted that the equations above only express contributions of each shape slope component in one direction to the overlay error component of the same direction. However, according to plate mechanics (a wafer deforms like a plate) there can be coupling between deformations in orthogonal directions. It is therefore contemplated that the accuracy and applicability of overlay error prediction can be further enhanced by the inclusion of higher order differential components and the removal of simple wafer bow components. Specifically, these components can be used to construct an overlay error predictor in a form of linear combination of these components or nonlinear combination of these components. This enhanced wafer-geometry induced overlay errors prediction method is shown in FIG. 10, and many different configurations can be constructed, depending on the predictor complexity requirements.

Figure 10:
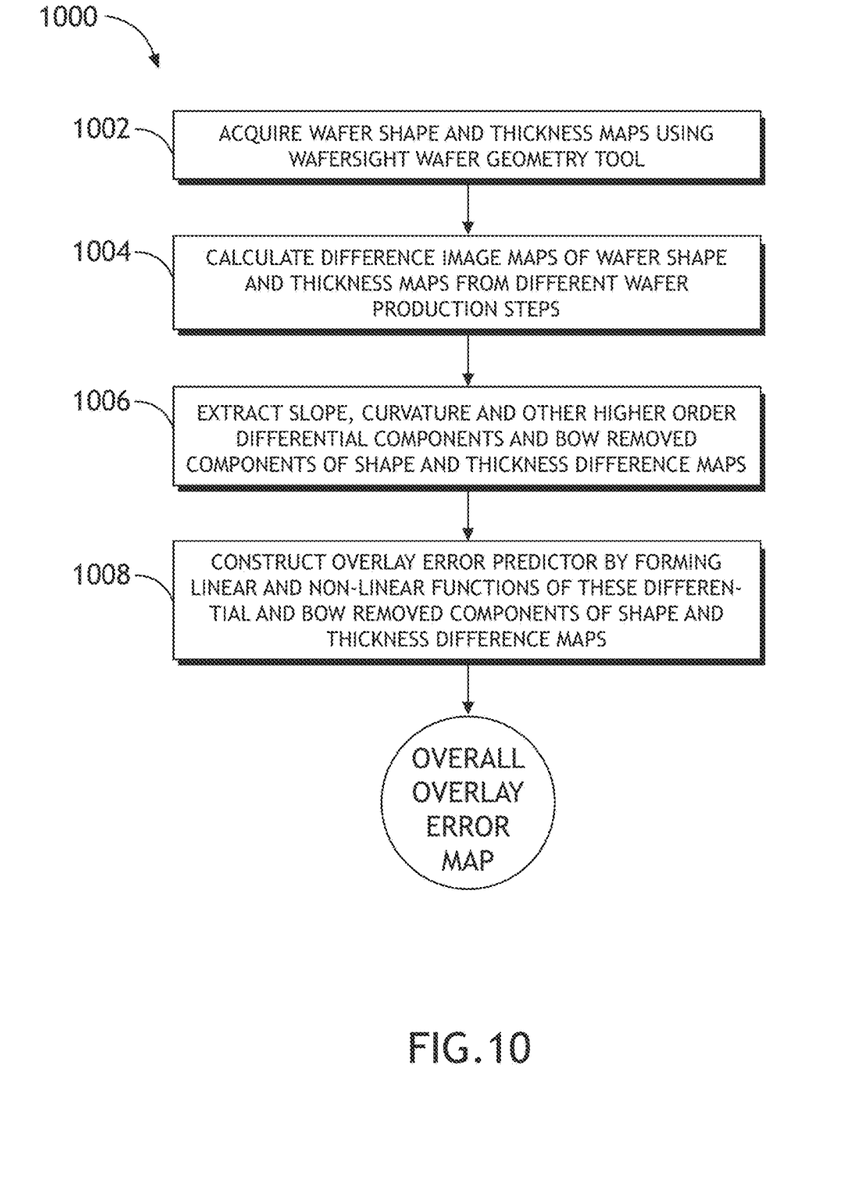
FIG. 10 is flow diagram depicting an enhanced wafer-geometry induced overlay errors prediction method.

As depicted in FIG. 10, in step 1002, wafer geometry and thickness data is acquired before and after the wafer is processed by a process tool. Difference maps (i.e., changes in wafer geometry and thickness) are calculated in step 1004. Subsequently, slope, curvature and other higher order differential components and bow removed components of shape and thickness difference maps can be extracted in step 1006. These additional components are taken into consideration in step 1008 to construct an enhanced overlay error predictor. For instance, one exemplary overlay error predictor can be constructed as:

$$OverlayError_x = a_{xx}SSCR_x + a_{xy}SSCR_y + b_{xx}CSC_x + b_{xy}CSC_y + c_{xx}SOSCR$$

$$OverlayError_y = a_{yx}SSCR_x + a_{yy}SSCR_y + b_{yx}CSC_x + b_{yy}CSC_y + c_{yy}SOSCR$$

Where the new components $CSC_x$ and $CSC_y$ are the curvature of shape change components in X and Y directions, respectively, SOSCR is the second order shape change residue component (e.g., the $2^{nd}$ order shape removal from the full shape), and the ten coefficients $a_{xx}$ to $c_{yy}$ are weighting coefficients. In these enhanced wafer-geometry induced overlay error predictors, in addition to incorporation of more shape difference components, the shape components obtained in one direction of X or Y are also used to provide the contribution in the prediction in its orthogonal directions Y or X. The improved prediction accuracy of overlay errors can be obtained as a result of incorporation of these wafer shape components.

It is noted that in the exemplary overlay error predictor defined above, the predicted overlay errors are linear combinations of the shape components, and all weighting coefficients are constant across the image spatial extent. It is contemplated that the overlay error predictors can also be constructed as weighted summations of the linear and non-linear functions of these shape components and more general spatial weighting patterns such as $a_{xx}(x,y)$ to $c_{yy}(x, y)$ have been found to provide effective further improvement in the prediction accuracy of overlay errors, since different spatial and magnitude contributions of the shape components help to compensate the spatial variant and nonlinear behavior of the overlay error in the overlay error formation mechanism. It is understood that whether to implement constant or variable weighting coefficients may be a design choice and specific implementations may vary without departing from the spirit and scope of the present disclosure.

It is also understood that additional components such as contributions from wafer thickness spatial variations and thickness differences at the same spatial positions resulting from two wafer processing stages may also be taken into consideration to further enhance overlay error prediction. These thickness variations can be utilized to work with various shape variation components in the enhanced overlay error predictors to better describe the wafer chucking process and improve the accuracy and coverage range of overlay error prediction in different wafer production use cases. It is contemplated that various other components not specifically mentioned above may also be included in the enhanced overlay error prediction.

It is contemplated that while some of the examples above referred to lithography tools, the systems and methods in accordance with the present disclosure are applicable to other types of process tools, which may also benefit from the focus error controls without departing from the spirit and scope of the present disclosure. In addition, film force based FE models in accordance with the embodiments of the present disclosure may also be configured to predict other errors such as focus errors (e.g., defocus) and the like. Furthermore, the term wafer used in the present disclosure may include a thin slice of semiconductor material used in the fabrication of integrated circuits and other devices, as well as other thin polished plates such as magnetic disc substrates, gauge blocks and the like.

The methods disclosed may be implemented in various wafer geometry measurement tools as sets of instructions executed by one or more processors, through a single production device, and/or through multiple production devices. Further, it is understood that the specific order or hierarchy of steps in the methods disclosed are examples of exemplary approaches. Based upon design preferences, it is understood that the specific order or hierarchy of steps in the method can be rearranged while remaining within the scope and spirit of the disclosure. The accompanying method claims present elements of the various steps in a sample order, and are not necessarily meant to be limited to the specific order or hierarchy presented.

It is believed that the system and method of the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory.

What is claimed is:

1. A method, comprising:
   obtaining a first set of wafer geometry measurements of a wafer prior to the wafer undergoing a fabrication process;
   obtaining a second set of wafer geometry measurements of the wafer after the wafer undergoes the fabrication process;
   calculating an initial film force distribution on the wafer based on the first set of wafer geometry measurements and the second set of wafer geometry measurements;
   calculating an additional film force distribution on the wafer at least partially based on the initial film force distribution;
   utilizing a finite element (FE) model to estimate a process-induced distortion of the wafer, wherein the FE model is utilized at least partially based on at least one of the initial film force distribution or the additional film force distribution; and
   adjusting one or more process tools of a semiconductor fabrication facility based on the estimated process-induced distortion, wherein the one or more process tools of the semiconductor fabrication facility include a first process tool implemented to fabricate the wafer, wherein the estimated process-induced distortion is provided to the first process tool via a feedback loop.

2. The method of claim 1, wherein the initial film force distribution is calculated as a product of a film stress and a film thickness.

3. The method of claim 2, wherein the film stress is determined at least partially based on the first set of wafer geometry measurements and the second set of wafer geometry measurements.

4. The method of claim 1, wherein the FE model is configured for:

generating a wafer model to represent at least one of one or more mechanical properties or a geometry of the wafer;

simulating one or more effects of the at least one of the initial film force distribution or the additional film force distribution on the wafer model; and calculating one or more out-of-plane distortions (OPD) based on the generated wafer model with the one or more simulated effects of the at least one of the initial film force distribution or the additional film force distribution.

5. The method of claim 1, wherein the FE model is configured for:

generating a wafer model to represent at least one of one or more mechanical properties or a geometry of the wafer;

simulating one or more effects of the at least one of the initial film force distribution or the additional film force distribution on the wafer model;

simulating one or more effects of wafer chucking on the wafer model; and calculating one or more in-plane distortions (IPD) based on the wafer model with the one or more simulated effects of the one or more simulated effects of wafer chucking and the at least one of the initial film force distribution or the additional film force distribution.

6. The method of claim 1, wherein the one or more process tools of the semiconductor fabrication facility include a second process tool, wherein the estimated process-induced distortion is provided to the second process tool via a feed forward loop, wherein the second process tool is adjustable via the estimated process-induced distortion.

7. The method of claim 1, wherein the calculating the additional film force distribution on the wafer at least partially based on the initial film force distribution comprises:

calculating a change in shape of the wafer based on the initial film force distribution and at least one of one or more calculated mechanical properties or a calculated geometry of the wafer; and comparing the calculated change in shape of the wafer against a measured change in shape of the wafer, wherein the calculate and compare processes are iteratively performed until a difference between the calculated change in shape of the wafer and the measured change in shape of the wafer is below a predetermined threshold.

8. The method of claim 1, further comprising:

obtaining a third set of wafer geometry measurements of the wafer after at least a second fabrication process;

calculating a second initial film force distribution on the wafer based on the second set of wafer geometry measurements and the third set of wafer geometry measurements; and utilizing the FE model to estimate at least a second process-induced distortion of the wafer, wherein the FE model is utilized at least partially based on the second initial film force distribution.

9. A method, comprising:

generating one or more basis film force distribution maps for a wafer;

performing finite element (FE) model based overlay error prediction for the one or more basis film force distribution maps, wherein the performing the FE model based overlay error prediction generates an overlay error prediction for the one or more basis film force distribution maps;

storing the one or more generated basis film force distribution maps;

storing the overlay error prediction generated for the stored one or more generated basis film force distribution maps;

forming a complete overlay error map of the wafer by:

synthesizing the overlay error prediction based on the one or more basis film force distribution maps to generate one or more overlay error contributions; and combining one or more overlay error contributions; and adjusting one or more process tools of a semiconductor fabrication facility based on the complete overlay error map, wherein the one or more process tools of the semiconductor fabrication facility include a first process tool implemented to fabricate the wafer, wherein the complete overlay error map is provided to the first process tool via a feedback loop.

10. The method of claim 9, wherein at least one of the generating the one or more basis film force distribution maps, the performing the FE model based overlay error prediction for the one or more basis film force distribution maps, the storing the one or more basis film force distribution maps, and the storing the overlay error prediction generated for the stored one or more basis film force distribution maps are part of an off-line training process, and are performed prior to and independently from the forming the complete overlay error map of the wafer.

11. The method of claim 9, wherein the one or more basis film force distribution maps includes at least one of one or more Zernike basis film force distribution maps or one or more Cosine basis film force distribution maps, wherein the at least some of the basis film force distribution maps of the one or more basis film force distribution maps include an image representing a film force distribution.

12. The method of claim 9, wherein the forming the complete overlay error map of the wafer comprises:

obtaining a first set of wafer geometry measurements of the wafer prior to the wafer undergoing a fabrication process;

obtaining a second set of wafer geometry measurements of the wafer after the wafer undergoes the fabrication process;

calculating a film force distribution of the wafer based on the first set of wafer geometry measurements and the second set of wafer geometry measurements;

decomposing the film force distribution of the wafer to a linear combination of one or more basis film force distribution maps; and synthesizing the generated overlay error prediction for the one or more basis film force distribution maps in the linear combination.

13. The method of claim 12, wherein the film force is calculated as a product of a film stress and a film thickness.

14. The method of claim 13, wherein the film stress is determined at least partially based on the first set of wafer geometry measurements and the second set of wafer geometry measurements.

15. The method of claim 9, wherein the one or more process tools of the semiconductor fabrication facility include a second process tool, wherein the complete overlay error map is provided to the second process tool via a feed forward loop, wherein the second process tool is adjustable via the complete overlay error map.

16. A system for providing distortion prediction for a wafer, the system comprising:

one or more geometry measurement tools, wherein the one or more geometry measurement tools obtains a first set of wafer geometry measurements of the wafer prior to the wafer undergoing a fabrication process, wherein the one or more geometry measurement tools obtains a second set of wafer geometry measurements of the wafer after the wafer undergoes the fabrication process; and a finite element (FE) model based prediction processor in communication with the geometry measurement tool, the FE model based prediction processor configured to:

calculate an initial film force distribution on the wafer based on the first set of wafer geometry measurements and the second set of wafer geometry measurements;

calculate an additional film force distribution on the wafer at least partially based on the initial film force distribution;

estimate a process-induced distortion of the wafer, wherein the FE model is utilized at least partially based on at least one of the initial film force distribution or the additional film force distribution; and adjust one or more process tools of a semiconductor fabrication facility based on the estimated process-induced distortion, wherein the one or more process tools of the semiconductor fabrication facility include a first process tool implemented to fabricate the wafer, wherein the estimated process-induced distortion is provided to the first process tool via a feedback loop.

17. The system of claim 16, wherein the initial film force distribution is calculated as a product of a film stress and a film thickness.

18. The system of claim 17, wherein the film stress is determined at least partially based on the first set of wafer geometry measurements and the second set of wafer geometry measurements.

19. The system of claim 16, wherein the FE model based prediction processor is further configured to:

generate a wafer model to represent at least one of one or more mechanical properties or a geometry of the wafer;

simulate one or more effects of the at least one of the initial film force distribution or the additional film force distribution on the wafer model; and calculate one or more out-plane distortions (OPD) based on the generated wafer model with the one or more simulated effects of the at least one of the initial film force distribution or the additional film force distribution.

20. The system of claim 16, wherein the FE model based prediction processor is further configured to:

generate a wafer model to represent at least one of one or more mechanical properties or a geometry of the wafer;

simulate one or more effects of the at least one of the initial film force distribution or the additional film force distribution on the wafer model;

simulate one or more effects of wafer chucking on the wafer model; and calculate one or more in-plane distortions (IPD) based on the wafer model with the one or more simulated effects of the one or more simulated effects of wafer chucking and the at least one of the initial film force distribution or the additional film force distribution.

21. The system of claim 16, wherein the FE model based prediction processor is further configured to:

calculate a change in shape of the wafer via the FE model based on the initial film force distribution and at least one of one or more calculated mechanical properties or a calculated geometry of the wafer; and compare the calculated change in shape of the wafer against a measured change in shape of the wafer, wherein the calculate and compare processes are iteratively performed until a difference between the calculated change in shape of the wafer and the measured change in shape of the wafer is below a predetermined threshold.

22. The system of claim 16, wherein the FE model based prediction processor is further configured to:

generate one or more basis film force distribution maps for the wafer;

perform finite element (FE) mod& based overlay error prediction for the one or more generated basis film force distribution maps, wherein the performing the FE model based overlay error prediction generates an overlay error prediction for the one or more basis film force distribution maps;

store the one or more generated basis film force distribution maps;

store the overlay error prediction generated for the stored one or more generated basis film force distribution maps; and form a complete overlay error map of the wafer by:

synthesizing the overlay error prediction based on the one or more basis film force distribution maps to generate one or more overlay error contributions; and combining one or more overlay error contributions; and provide the complete overlay error map of the wafer to adjust one or more process tools of a semiconductor fabrication facility.

23. The system of claim 22, the FE model based overlay error prediction for the one or more generated basis film force distribution maps is performed in an off-line training process.

24. The system of claim 23, wherein the FE model based prediction processor is further configured to:

decompose the at least one of the initial film force distribution or the additional film force distribution of the wafer to a linear combination of one or more basis film force distribution maps; and synthesize the generated overlay error prediction for the one or more basis film force distribution maps in the linear combination.

25. The system of claim 24, wherein the one or more basis film force distribution maps includes at least one of one or more Zernike basis film force distribution maps or one or more Cosine basis film force distribution maps, wherein the at least some of the basis film force distribution maps of the one or more basis film force distribution maps are an image representing a film force distribution.

* * * * *